US011179530B1

(12) United States Patent
Corey (10) Patent No.: US 11,179,530 B1
(45) Date of Patent: Nov. 23, 2021

(54) THERAPEUTIC ENDOTRACHEAL SYSTEM (71) Applicant: Matthew Corey, Phoenix, AZ (US)

(72) Inventor: Matthew Corey, Phoenix, AZ (US)

(73) Assignee: New Treatment Horizons, LLC, Phoenix, AZ (US)

( * ) Notice: Subject to any disclaimer, the term of this patent is extended or adjusted under 35 U.S.C. 154(b) by 0 days.

(21) Appl. No.: 17/144,112

(22) Filed: Jan. 7, 2021

Related U.S. Application Data

(60) Provisional application No. 63/104,903, filed on Oct. 23, 2020.

(51) Int. Cl.
*A61M 16/04* (2006.01)
*A61N 5/06* (2006.01)
*A61B 18/22* (2006.01)

(52) U.S. Cl.
CPC .... *A61M 16/0402* (2014.02); *A61M 16/0486* (2014.02); *A61B 2018/2238* (2013.01); *A61M 16/0434* (2013.01); *A61M 2205/053* (2013.01); *A61M 2205/587* (2013.01); *A61N 5/0624* (2013.01); *A61N 2005/063* (2013.01); *A61N 2005/0604* (2013.01); *A61N 2005/0643* (2013.01); *A61N 2005/0661* (2013.01)

(58) Field of Classification Search
CPC .............. A61M 16/04; A61M 16/0402; A61M 16/0434; A61M 16/0465; A61M 16/0468; A61M 16/0475; A61M 16/0486; A61M 46/0488; A61M 25/0021; A61M 25/0026; A61M 2025/0004; A61M 25/0009; A61M 25/0041; A61M 25/09; A61M 2025/09125; A61M 25/0925; A61N 5/06; A61N 5/0601; A61N 2005/0602; A61N 5/0603; A61N 2005/0604; A61N 2005/0606; A61N 2005/0609; A61N 2005/061; A61N 2005/0626; A61N 2005/0627; A61N 2005/063; A61N 2005/0632; A61N 2005/0643; A61N 2005/065; A61N 2005/0651; A61N 2005/0661; A61F 2/04; A61F 2002/043; A61F 2002/046
USPC ..... 606/2.5, 3, 7, 10, 11, 13–15; 607/88, 89, 607/92, 94
See application file for complete search history.

(56) References Cited

U.S. PATENT DOCUMENTS

| | | | | |
|---|---|---|---|---|
| 5,819,723 | A * | 10/1998 | Joseph | A61M 16/044 128/207.14 |
| 7,322,357 | B2 * | 1/2008 | Nelson | A61M 16/04 128/207.14 |
| 2014/0150782 | A1 * | 6/2014 | Vazales | A61M 16/0463 128/202.16 |

(Continued)

*Primary Examiner* — Ahmed M Farah
(74) *Attorney, Agent, or Firm* — KW Law, LLP (57) ABSTRACT

A therapeutic intubation device may comprise a tube, a first probe channel, a second probe channel, a first probe and a second probe. In various embodiments, a tube may have an elongate body having a proximal end and a distal end. The body may define a first channel between the proximal end and the distal end. A first probe channel may be defined in the body. A second probe channel defined in the body. A first probe may comprise a first body portion and a first end portion, the first end portion comprising a first ultraviolet-c ("UVC") light emitting device. The first probe may be installable the first probe channel such that the first end portion of the first probe is adjacent the distal end of the tub during operation.

20 Claims, 5 Drawing Sheets

(56) References Cited

U.S. PATENT DOCUMENTS

2014/0275772 A1* 9/2014 Chuda .................... A61B 1/267
                                                    600/104
2016/0296719 A1* 10/2016 Geraghty .......... A61M 16/0486

* cited by examiner

THERAPEUTIC ENDOTRACHEAL SYSTEM

CROSS REFERENCE TO RELATED APPLICATION

The present application claims priority to and the benefit of U.S. provisional patent application Ser. No. 63/104,903 filed on Oct. 23, 2020, which are hereby incorporated by reference in their entirety for any purpose.

FIELD

The present disclosure relates to endotracheal tubes. More specifically, the present disclosure relates to endotracheal tubes with therapeutic structures to treat internal volumes of an anatomy (e.g., the lungs of a human or animal).

BACKGROUND

There is a need to treat lung tissue that has been compromised by bacteria or virus. In light of the COVID-19 pandemic, the needs for therapeutic lung treatment in healthy and unhealthy patients has increased dramatically all over the world. With the various traditional treatments being ineffective for some patients suffering from COVID-19, the need to treat infected tissue directly has also significantly increased.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

SUMMARY

In various embodiments, a therapeutic intubation device may comprise a tube, a first probe, a second probe and a controller. The tube may have an elongate body having a proximal end and a distal end. The body may define a first channel, between the proximal end and the distal end. The body may also define a second channel along a length of the body and a third channel along the length of the body. The first probe may comprise first body portion. The first body portion may comprise a first proximal end and a first distal end. The first body portion may also comprise a first trigger operatively coupled to the proximal end of the first body portion. The first trigger portion configured to move the distal end, and a first ultraviolet-c ("UVC") light emitting device disposed at a distal portion of the first body portion, the first probe installable in the second channel of the tube.

In various embodiments, a therapeutic intubation device may comprise a second probe comprising second body portion comprising a second proximal end and a second distal end, a second trigger may be operatively coupled to the proximal end of the second body portion. The second probe may be configured to move the distal end, and a second UVC light emitting device disposed at the distal end of the second body portion, the second probe may be installable in the third channel of the tube.

In various embodiments, a therapeutic intubation device may comprise a controller configured to control the emission of UVC light from at least one of the first UVC light emitting device and the second UVC light emitting device. In various embodiments, a therapeutic intubation device may comprise a light emitting device. The light emitting device may be a solid-state device. In various embodiments, the light emitting device is a diode.

In various embodiments, a therapeutic intubation device may comprise a controller configured to control the exposure time, exposure profile and wavelength of the UVC light. In various embodiments, a therapeutic intubation device may comprise a controller configured to control exposure time is 3 to 5 seconds.

In various embodiments, a therapeutic intubation device may comprise a controller configured to control an exposure profile that is a pulsatile profile, an on-off profile, or a steady state profile.

In various embodiments, a therapeutic intubation device may comprise a controller configured to deliver a UVC between about a wavelength of 200-280 nm.

In various embodiments, a therapeutic intubation device may comprise a tube, a first probe channel, a second probe channel, a first probe and a second probe. In various embodiments, a tube may have an elongate body having a proximal end and a distal end. The body may define a first channel between the proximal end and the distal end. A first probe channel may be defined in the body. A second probe channel defined in the body. A first probe may comprise a first body portion and a first end portion, the first end portion comprising a first ultraviolet-c ("UVC") light emitting device. The first probe may be installable the first probe channel such that the first end portion of the first probe is adjacent the distal end of the tub during operation. In various embodiments, a second probe may comprise a second body portion and a second end portion, the second end portion comprising a second UVC light emitting device. In various embodiments, the second probe installable the second probe channel such that the second end portion of the second probe is adjacent the distal end of the tub during operation.

In various embodiments, wherein the therapeutic intubation device may comprise a controller configured to control a power supply. In various embodiments, wherein the therapeutic intubation device may comprise a light emitting device is a solid state device. In various embodiments, wherein the therapeutic intubation device may comprise the light emitting device is a diode. In various embodiments, wherein the therapeutic intubation device may comprise first probe comprises a trigger. The trigger may manipulate the first end in the first probe channel relative to the tube. The trigger may be configured to point the first end portion.

In various embodiments, therapeutic intubation device or system may further comprising a controller. The controller may be configured to power the first probe. The controller may be configured to control the exposure time of the UVC light. The controller may be configured to control the exposure profile of the UVC light. The controller may also be configured to control the wavelength of the UVC light. For example, and in various embodiments, the exposure time of the UVC light provided by the therapeutic intubation device or system may be 3 to 5 seconds. In various embodiments, the exposure profile of the UVC light provided by the therapeutic intubation device or system may be a pulsatile profile. In various embodiments, the exposure profile of the UVC light provided by the therapeutic intubation device or system may be an on-off profile. In various embodiments, the exposure profile of the UVC light provided by the therapeutic intubation device or system may be a steady state profile.

In various embodiments, the wavelength of the UVC light provided by the therapeutic intubation device or system may be 200-280 nm. In various embodiments, the wavelength of the UVC light provided by the therapeutic intubation device or system may be 250-270 nm. In various embodiments, the wavelength of the UVC light provided by the therapeutic intubation device or system may be 262 nm.

In various embodiments, the exposure time of the UVC light provided by the therapeutic intubation device or system may be approximately 15 to 30 seconds. In various embodiments, the exposure time of the UVC light provided by the therapeutic intubation device or system may be approximately 1 to 3 seconds. In various embodiments, the exposure time of the UVC light provided by the therapeutic intubation device or system may be approximately 4 to 14 seconds.

In various embodiments, the first UVC light emitting device or the second UVC light emitting device may be a light emitting fiber. In various embodiments, wherein light emitting fiber may be covered by a perforated or retractable cover or sheath.

DETAILED DESCRIPTION

The detailed description of exemplary embodiments herein refers to the accompanying drawings, which show exemplary embodiments by way of illustration. While these exemplary embodiments are described in sufficient detail to enable those skilled in the art to practice the inventions, other embodiments may be realized, and that logical, chemical and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Figure 1:
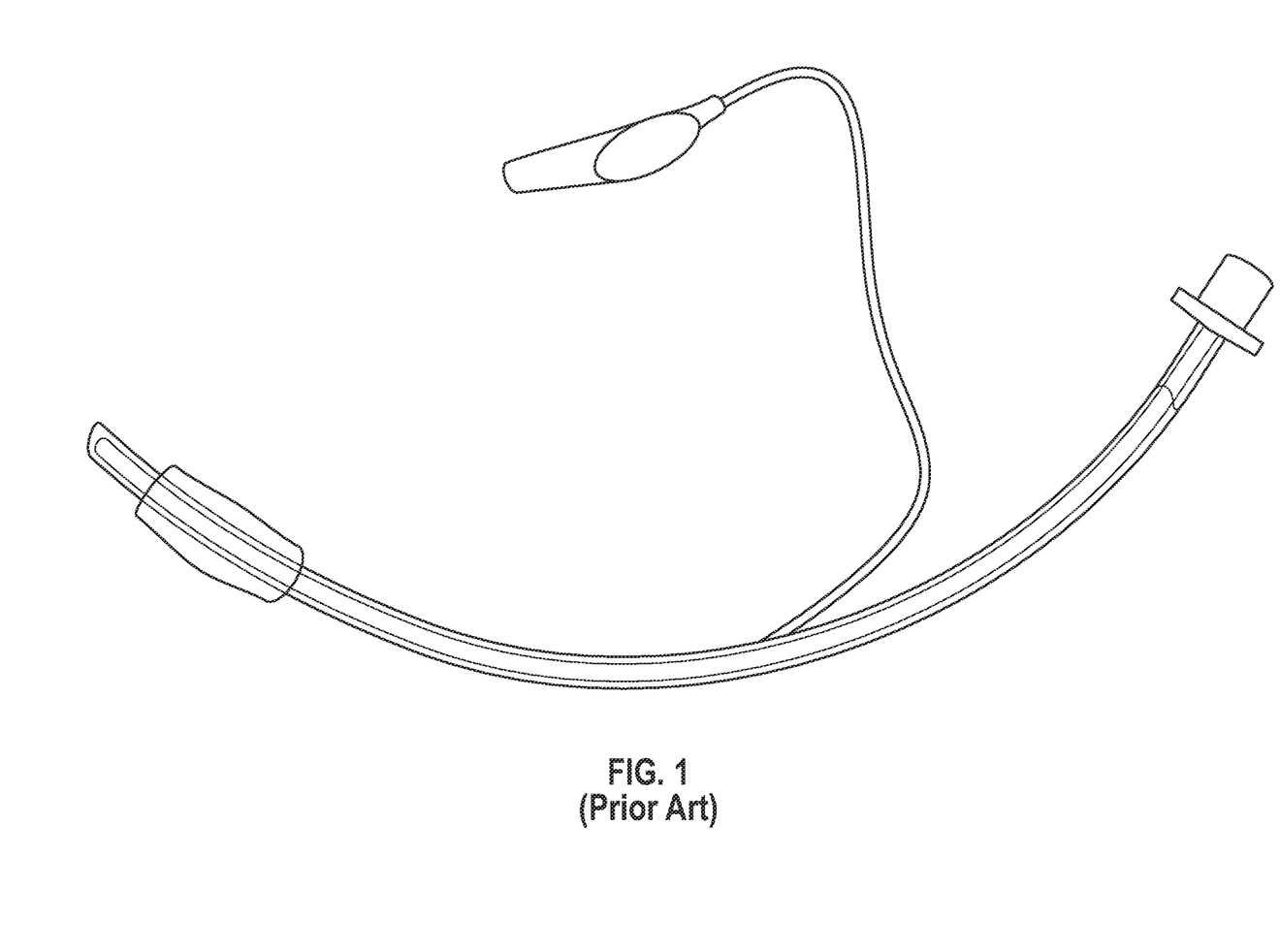
FIG. 1 illustrates a side view of a prior art endotracheal tube.

FIG. 1 shows a prior art endotracheal tube that includes various features, in endotracheal tube construction. For example, FIG. 1 includes a tube body with length markings and a connector. FIG. 1 also includes a cuff and pilot balloon system with a pilot line and a one-way valve.

Figure 2:
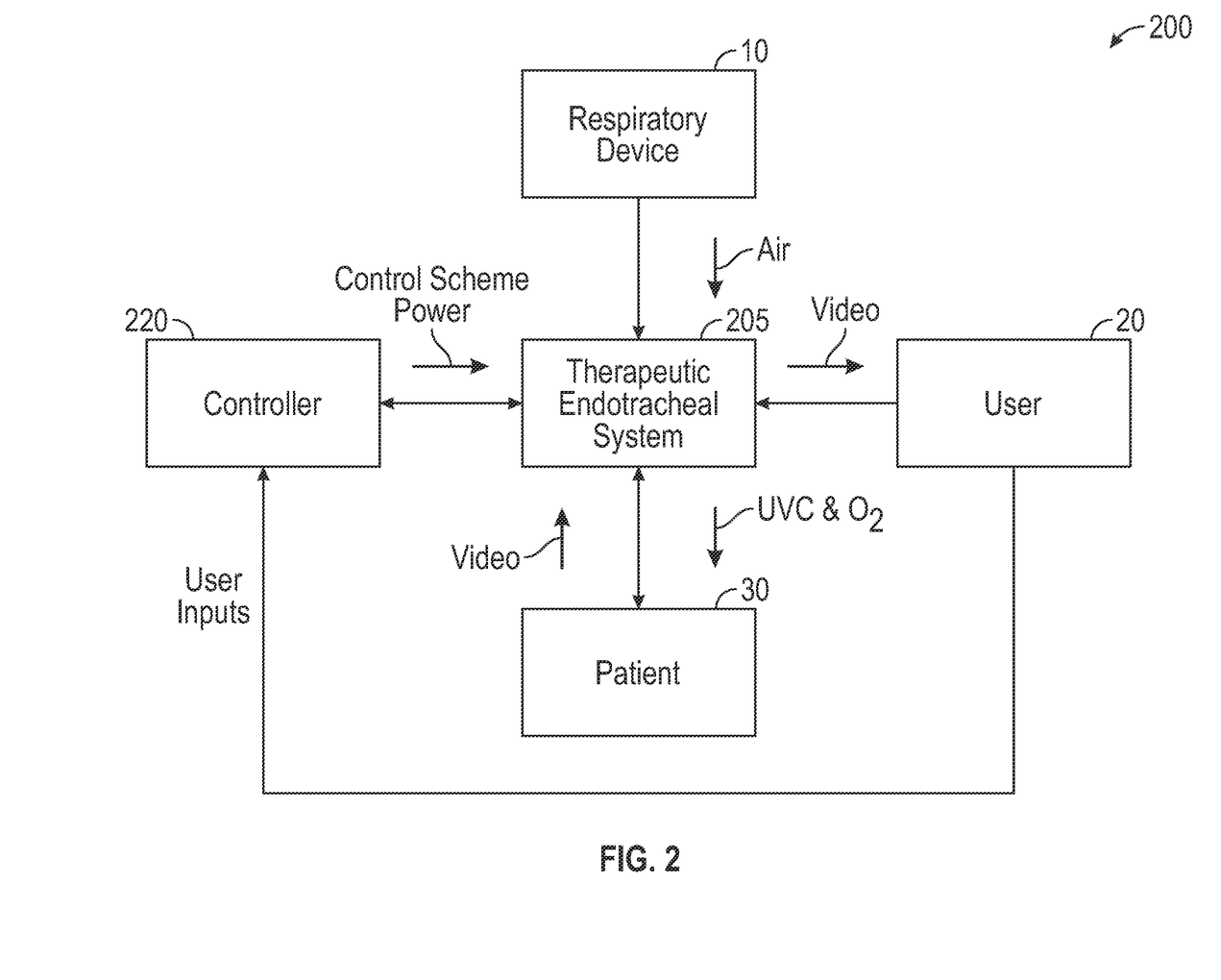
FIG. 2 illustrates a block diagram of the therapeutic endotracheal treatment system, in accordance with various embodiments.

In various embodiments and with reference to FIG. 2, a therapeutic intubation system 200 may comprise an intubation tube 205 and a controller 220. Therapeutic intubation system 200 may also comprise and/or receive inputs (e.g., oxygen or air) from a respiratory device 10 (e.g., a ventilation bag, a ventilator, and/or the like). Therapeutic intubation system 200 may also receive inputs from a user 20 via controller 220 or respiratory device 10.

In various embodiments, controller 220 may be configured to provide power to therapeutic endotracheal system 205. Controller 220 may also be configured to deliver a control scheme to therapeutic endotracheal system 205. The control scheme may include an exposure time. The control scheme may include an exposure profile. The control scheme may include a wavelength of UVC light.

In various embodiments, the control scheme may include any suitable amount of exposure time defined by a user or course of treatment programmed in controller 220. Exposure time may be the time a dose of UVC light is exposed to a patient's anatomy (e.g., a patient's lungs). For example, the exposure time may be 3 to 5 seconds. In another example, the exposure time my to 15 to 30 seconds. In another example, the exposure time my to 4 to 14 seconds. In yet another example, the exposure time my to 1 to 3 seconds. Exposure time may be adjusted by on a therapeutic scheme with other variable including exposure profile, the wavelength of the UVC light and the conditions of the patient's anatomy or lungs.

In various embodiments, the control scheme may include any exposure profile defined by a user or course of treatment programmed in controller 220. Exposure profile may be the cadence, tempo, or tone of the UVC light while it is exposed to a patient's anatomy (e.g., a patient's lungs). For example, the exposure profile may be pulsatile profile. In another example, the exposure profile may be an on-off profile. In yet another example, the exposure profile may be an steady state profile.

In various embodiments, the control scheme may include any suitable wavelength of UVC light defined by a user or course of treatment programmed in controller 220. For example, the wavelength of the UVC light may be 200-280 nm. In another example, the wavelength of the UVC light may be 250-270 nm. In another example, the wavelength of the UVC light may be 255-265 nm. In yet another example, the wavelength of the UVC light may be 262 nm.

Figure 3A:
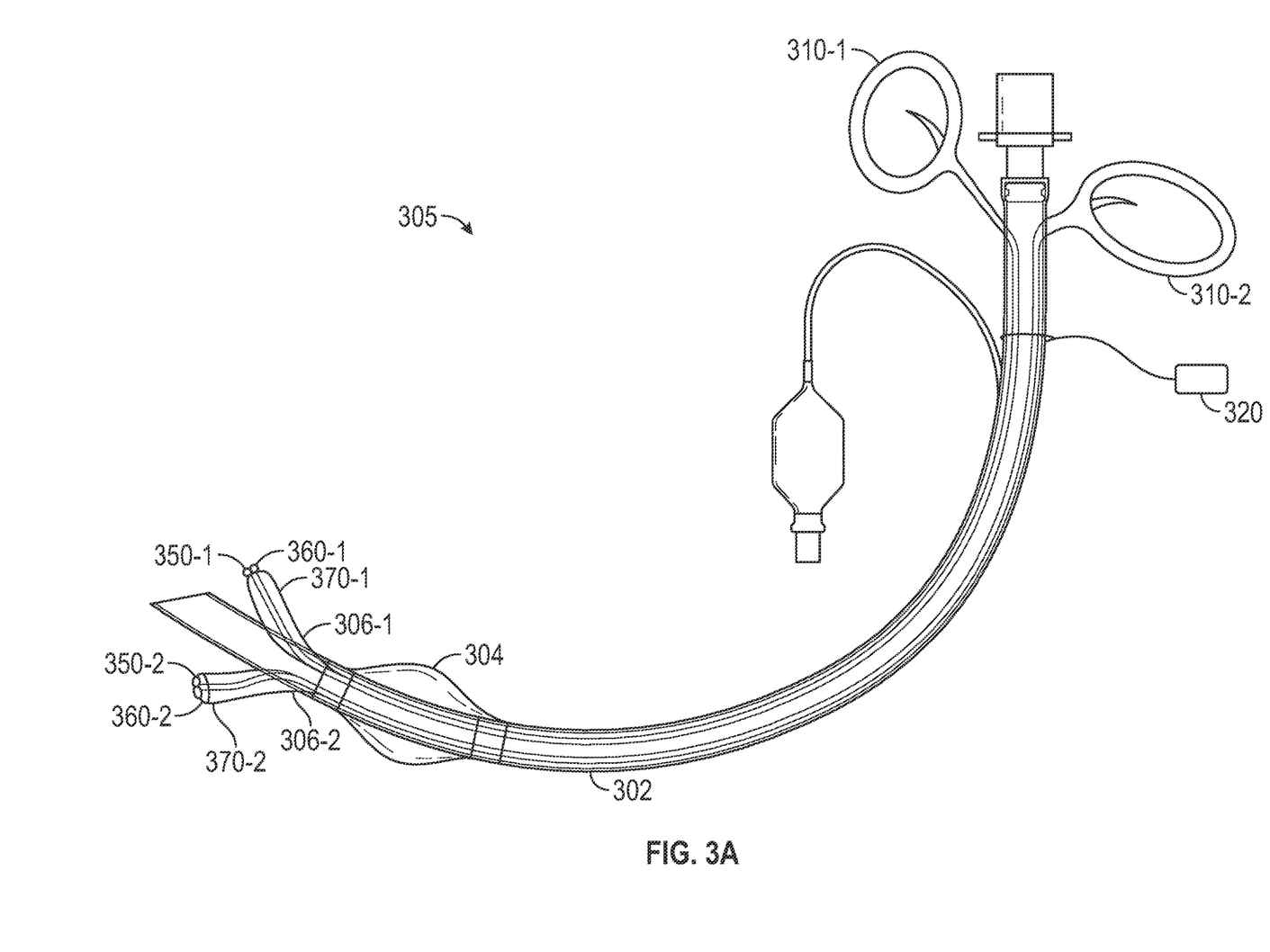
FIG. 3A illustrates a side view of a therapeutic endotracheal tube in a first position, in accordance with various embodiments.
Figure 3B:
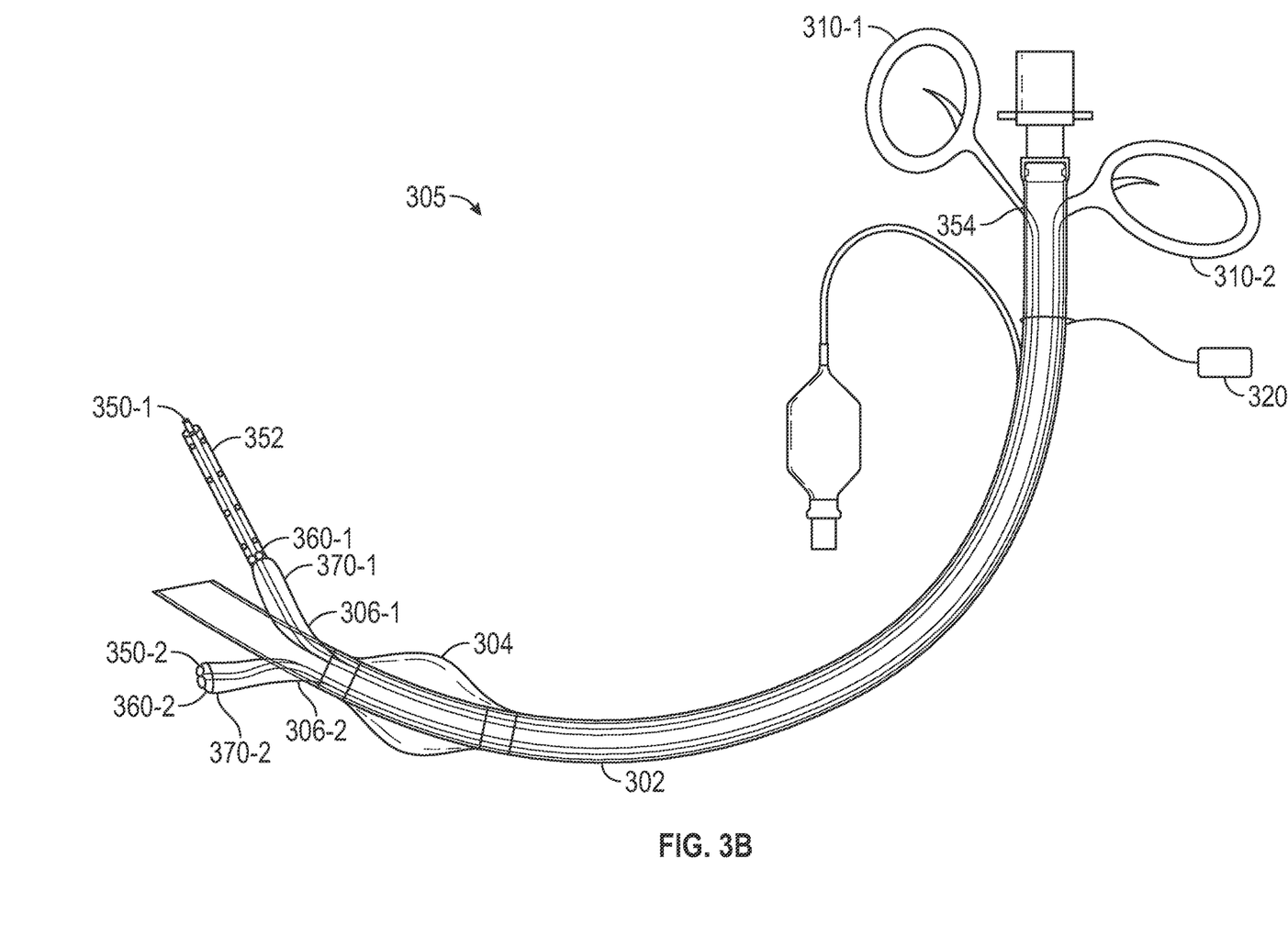
FIG. 3B illustrates a side view of a therapeutic endotracheal tube in a second position, in accordance with various embodiments.

In various embodiments and with reference to FIG. 3A and FIG. 3B, a therapeutic intubation device 305 may comprise any suitable features including any or all of the features shown and described in FIG. 1, any feature found in a typical endotracheal tube assembly, and/or the like.

In various embodiments, therapeutic intubation device 305 may comprise a body 302 having a proximal end, a distal end, and a channel defined between the proximal end and the distal end. Therapeutic intubation device 305 may comprise a cuff or balloon 304 that is inflatable in response to being placed in patient's airway. Cuff 304 may be located in a distal portion of body 302. Therapeutic intubation device 305 may also comprise directional outlets 306-1 and/or 306-2 in the distal portion of body 302 and distantly adjacent to cuff 304. Body 302 may comprise one or more channel portions defined along a length of body 302. The channel portion may be separately defined in the channel between the proximal and distal end of body 302. The channel portions may be configured to receive and allow one or more therapeutic devices to be inserted into a channel portion and run along the length of body 302 to directional outlets 306-1 and/or 306-2.

In various embodiments, therapeutic intubation device 305 may comprise a trigger system 310 (e.g., trigger system 310-1, trigger system 310-2, and/or the like). Trigger system 310 may be installed through a proximal end of the one or more channel portions. Therapeutic intubation device 305 may also comprise an ultraviolet-c (UVC) light system 350-1 and/or 350-2. UVC light system 350-1 and/or 350-2 may be installed through the one or more channel portions and may protrude through directional outlets 306-1 and/or 306-2 in response to being deployed in the patient. Therapeutic intubation device 305 may further comprise a camera 360-1 and/or 360-2. Like UVC light system 350-1 and/or 350-2, camera 360-1 and/or 360-2 may be installable through the one or more channel portions and may protrude through directional outlets 306-1 and/or 306-2 in response to being deployed in a patient. Therapeutic intubation device 305 may also comprise a wire 370-1 and/or 370-2. Similar to UVC light system 350-1 and/or 350-2 and camera 360-1 and/or 360-2, wire 370-1 and/or 370-2 may be installable through the one or more channel portions and may protrude through directional outlets 306-1 and/or 306-2 in response to being deployed in a patient. Trigger system 310 may be configured to actuate wire 370-1 and/or 370-2 to manipulate the position and or direction of UVC light system 350-1 and/or 350-2, camera 360-1 and/or 360-2, and/or any other suitable structures.

In various embodiments and with reference to FIG. 3B, UVC light system 350 may be a fiber. UVC light system 350 may also be covered with the sheath 352. Sheath 352 may be retractable along a length of UVC light system 350. For example, sheath 352 may be retractable by actuating a retraction system 354 (e.g., a wire or other suitable structure). Sheath 352 may also be partial or fully perforated. In this regard, sheath 352 may defined one or more holes that allow light to be transmitted to a patient's anatomy while the sheath 352 is not retracted or partially retracted. Sheath 352 may also allow the user to control or further manipulate exposure time or an exposure profile.

In various embodiments, UVC light system 350 may be any suitable light system. UVC light system 350 may be a solid-state device or fiber. In this regard, a length of distal portion of UVC light system 350 may be configured to emit UVC light. UVC light system 350 may include a perforated cover that is retractable by a user.

Figure 4:
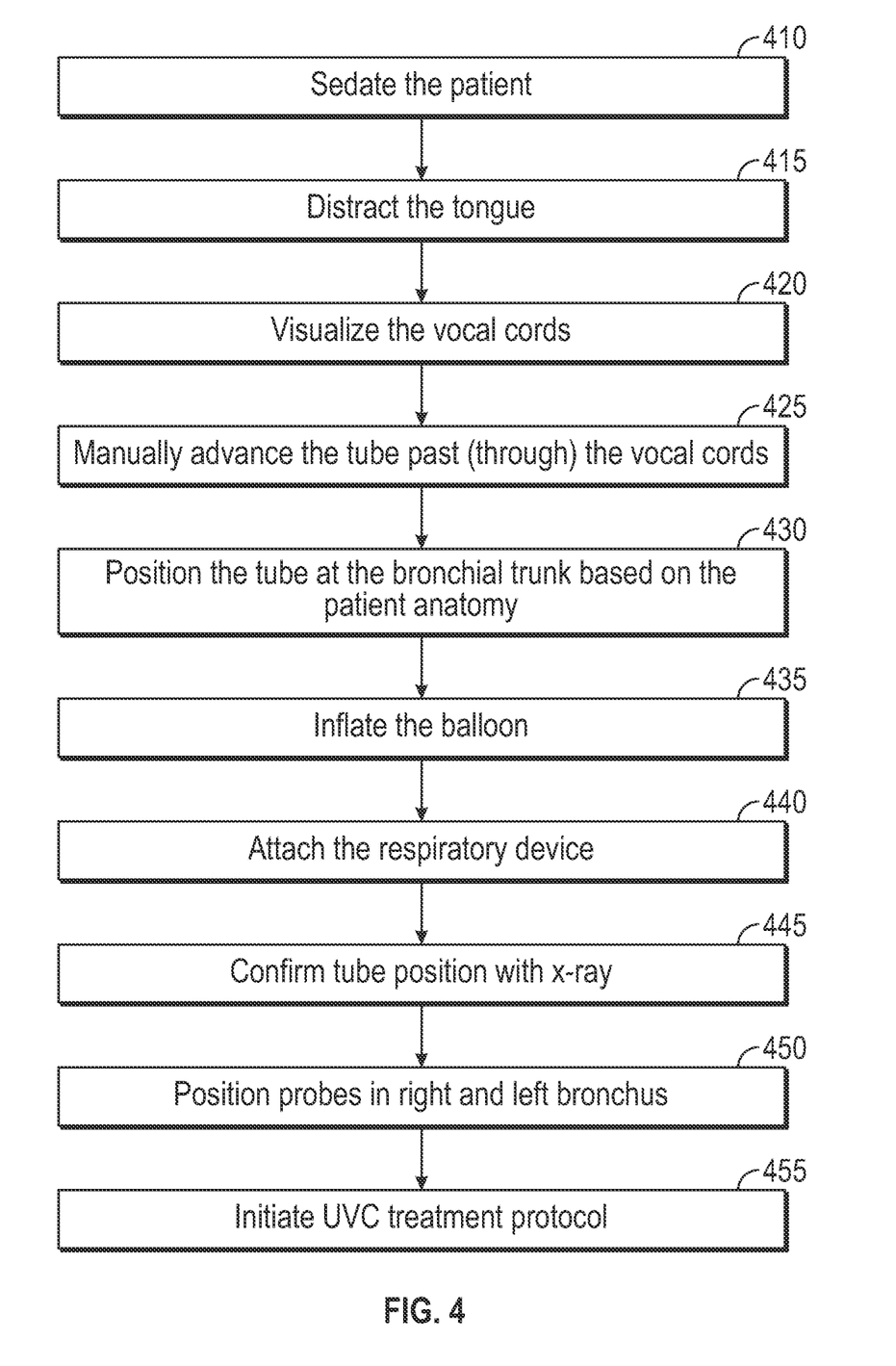
FIG. 4 illustrates a method of operating the therapeutic endotracheal treatment system, in accordance with various embodiments.

In various embodiments and with reference to FIG. 4, a method of treating a patient's lungs with UVC light is provided. The method requires preparation and intubation of the patient. To prepare the patient, a user (e.g., a medical professional) must sedate the patient (Step 410). The user may then distract (i.e., move or displace) the tongue (Step 415). The user may then visualize the vocal cords (Step 420). As this method of treatment is generally directed a non-emergency procedure, the patient mouth and airway may be generally free from debris or obstruction. The user may manually advance the tube (e.g., the therapeutic intubation device described herein) past and/or through the vocal cords (Step 425). The user may then position the tube (e.g., the therapeutic intubation device described herein) at the bronchial trunk based on the patient anatomy (Step 430). The user may inflate the balloon in toward the distal end of the tube (Step 435).

In various embodiments, the user may attach a respiratory device (e.g., a respirator bag, a ventilator, and/or the like) (Step 440). The user may inspect the patient anatomy for breadth sounds or to see the patient's chest rise and fall. The position of the tube may be confirmed with an x-ray (Step 445). The probes (e.g., the probes included in the UVC light system of therapeutic intubation device described herein) may be positioned in the left and right bronchus (Step 450). The user or controller may then initiate a UVC treatment protocol with the structures, exposure time, exposure profiles, and wavelengths of light described herein.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A therapeutic intubation device, comprising:
a tube having an elongate body having a tube proximal end and a tube distal end, the elongate body defining a first channel, between the tube proximal end and the tube distal end, a second channel along a length of the elongate body and a third channel along the length of the elongate body;
a first probe comprising first body portion comprising a first probe proximal end and a first probe distal end, a first trigger operatively coupled to the probe proximal end of the first body portion and configured to move the probe distal end, and a first ultraviolet-c ("UVC") light emitting device disposed at a first probe distal portion of the first body portion, the first probe configured to be installed in the second channel of the tube, in response to actuation of the first probe and first trigger by a user, the probe distal end and the first UVC light emitting device is configured to be positioned beyond the tube distal end in a first bronchus of a patient;

a second probe comprising second body portion comprising a second probe proximal end and a second probe distal end, a second trigger operatively coupled to the second probe proximal end of the second body portion and configured to move the second probe distal end, and a second UVC light emitting device disposed at the second probe distal end of the second body portion, the second probe configured to be installed in the third channel of the tube, in response to actuation of the second probe and the second trigger by the user, the probe distal end and the second UVC light emitting device is configured to be positioned beyond the tube distal end in a second bronchus of the patient; and probe and the second trigger by the user, the probe distal end and the second UVC light emitting device is configured to be positioned beyond the tube distal end in a second bronchus of the patient.

2. The therapeutic intubation device of claim 1, wherein the controller is configured to control an exposure time, an exposure profile and a wavelength of UVC light.

3. The therapeutic intubation device of claim 2, wherein the exposure time is 3 to 5 seconds.

4. The therapeutic intubation device of claim 2, wherein the exposure profile is a pulsatile profile, an on-off profile, or a steady state profile.

5. The therapeutic intubation device of claim 2, wherein the wavelength is 250-270 nm.

6. The therapeutic intubation device of claim 1, wherein the first UVC light emitting device is a solid state device.

7. The therapeutic intubation device of claim 1, wherein the first UVC light emitting device or the second UVC light emitting device is a light emitting fiber and wherein the light emitting fiber is covered by a perforated sheath.

8. A therapeutic intubation device, comprising:
  a tube having an elongate body having a proximal end and a distal end, the elongate body defining a first channel between the proximal end and the distal end;
  a first probe channel defined in the elongate body;
  a second probe channel defined in the elongate body;
  a first probe comprising a first body portion and a first end portion, the first end portion comprising a first ultraviolet-c ("UVC") light emitting device, the first probe configured to be installed in the first probe channel such that the first end portion of the first probe is adjacent the distal end of the tub during operation, in response to actuation of the first probe and first trigger by a user, the probe distal end and the first UVC light emitting device is configured to be positioned beyond the tube distal end in a first bronchus of a patient; and
  a second probe comprising a second body portion and a second end portion, the second end portion comprising a second UVC light emitting device, the second probe configured to be installed in the second probe channel such that the second end portion of the second probe is adjacent the distal end of the tube during operation, in response to actuation of the second probe and second trigger by the user, the probe distal end and the second UVC light emitting device is configured to be positioned beyond the tube distal end in a second bronchus of the patient.

9. The therapeutic intubation device of claim 8, wherein the first probe comprises a trigger and wherein the trigger manipulates the first end portion in the first probe channel relative to the tube.

10. The therapeutic intubation device of claim 8, wherein the second probe comprises a trigger and wherein the trigger manipulates the second end portion in the second probe channel relative to the tube.

11. The therapeutic intubation device of claim 5, further comprising a controller.

12. The therapeutic intubation device of claim 11, wherein the controller is configured to power the first probe.

13. The therapeutic intubation device of claim 11, wherein the controller is configured to control an exposure time, an exposure profile and a wavelength of UVC light.

14. The therapeutic intubation device of claim 13, wherein the exposure profile is pulsatile profile, an on-off profile, or a steady state profile.

15. The therapeutic intubation device of claim 13, wherein the wavelength is 200-280 nm.

16. The therapeutic intubation device of claim 13, wherein the wavelength is 262 nm.

17. The therapeutic intubation device of claim 13, wherein the exposure time is 15 to 30 seconds.

18. The therapeutic intubation device of claim 13, wherein the exposure time is 1 to 3 seconds.

19. The therapeutic intubation device of claim 13, wherein the exposure time is 4 to 14 seconds.

20. A therapeutic intubation device, comprising:
  a tube having an elongate body having a proximal end and a distal end, the elongate body defining a first channel, between the proximal end and the distal end, a second channel along a length of the elongate body and a third channel along the length of the elongate body;
  a first probe comprising first body portion comprising a first proximal end and a first distal end, a first trigger operatively coupled to the proximal end of the first body portion and configured to move the distal end, and a first ultraviolet-c ("UVC") light emitting device disposed at a distal portion of the first body portion, the first probe configured to be installed in the second channel of the tube,
  wherein the first UVC light emitting device is a solid state device;
  a second probe comprising second body portion comprising a second proximal end and a second distal end, a second trigger operatively coupled to the proximal end of the second body portion and configured to move the distal end, and a second UVC light emitting device disposed at the distal end of the second body portion, the second probe configured to be installed in the third channel of the tube,
  wherein the first UVC light emitting device or the second UVC light emitting device is a light emitting fiber and wherein the light emitting fiber is covered by a perforated sheath; and
  a controller configured to control emission of UVC light from at least one of the first UVC light emitting device and the second UVC light emitting device,
    wherein the controller is configured to control an exposure time, an exposure profile and a wavelength of UVC light, and
    wherein the wavelength is 250-270 nm.

* * * * *